(12) United States Patent
McCraty et al.

(10) Patent No.: US 8,764,673 B2
(45) Date of Patent: Jul. 1, 2014

(54) SYSTEM AND METHOD FOR FACILITATING GROUP COHERENCE

(75) Inventors: Rollin McCraty, Boulder Creek, CA (US); Doc L. Childre, Boulder Creek, CA (US); Michael A. Atkinson, Boulder Creek, CA (US)

(73) Assignee: Quantum Intech, Inc., Boulder Creek, CA (US)

( * ) Notice: Subject to any disclaimer, the term of this patent is extended or adjusted under 35 U.S.C. 154(b) by 974 days.

(21) Appl. No.: 12/506,788

(22) Filed: Jul. 21, 2009

(65) Prior Publication Data

US 2009/0281400 A1    Nov. 12, 2009

Related U.S. Application Data

(63) Continuation-in-part of application No. 12/264,138, filed on Nov. 3, 2008, now Pat. No. 8,066,637, which is a continuation of application No. 11/528,955, filed on Sep. 27, 2006, now Pat. No. 7,462,151, which is a continuation of application No. 10/486,775, filed as application No. PCT/US00/05224 on Mar. 1, 200, now Pat. No. 7,163,512, which is a continuation of application No. 09/260,643, filed on Mar. 2, 1999, now Pat. No. 6,358,201.

(60) Provisional application No. 61/084,353, filed on Jul. 29, 2008.

(51) Int. Cl.
*A61B 5/0452* (2006.01)

(52) U.S. Cl.
USPC .......................................... 600/508; 600/509

(58) Field of Classification Search
USPC .................................................. 600/508–509
See application file for complete search history.

(56) References Cited

U.S. PATENT DOCUMENTS

| | | | | |
|---|---|---|---|---|
| 6,358,201 B1 * | 3/2002 | Childre et al. | ................ | 600/300 |
| 7,163,512 B1 * | 1/2007 | Childre et al. | ................ | 600/500 |
| 2004/0229685 A1 * | 11/2004 | Smith et al. | ...................... | 463/29 |
| 2007/0270668 A1 | 11/2007 | Childre et al. | | |
| 2008/0020848 A1 | 1/2008 | Muir et al. | | |

* cited by examiner

*Primary Examiner* — Paula J Stice
(74) *Attorney, Agent, or Firm* — K&L Gates LLP

(57) ABSTRACT

Group coherence is facilitated in a group environment, such as a gaming, competitive, cooperative or collaborative environment. In one embodiment, a graphical representation of a scenario may be presented to a plurality of individuals. A physiological measure for each of the plurality of individuals may be sampled and used to track the individuals' heart rhythm patterns. A current group coherence level for the plurality of individuals may then be determined, where the group coherence level corresponds to a collective degree to which said plurality of heart rhythm patterns exhibit a sine waveform. In one embodiment, an appropriate modification to the scenario may be determined, where the modification is based on the current group coherence level. The updated graphical representation of the scenario may then be presented to the plurality of individuals.

39 Claims, 4 Drawing Sheets

SYSTEM AND METHOD FOR FACILITATING GROUP COHERENCE

CROSS-REFERENCE TO RELATED APPLICATIONS

This application claims the benefit of U.S. Provisional Application No. 61/084,353 filed on Jul. 29, 2008. This application is also a continuation-in-part of application Ser. No. 12/264,138 filed on Nov. 3, 2008, which is a continuation of application Ser. No. 11/528,955 filed on Sep. 27, 2006 (now U.S. Pat. No. 7,462,151), which is a continuation application of application Ser. No. 10/486,775, which is the National Stage of International Application No. PCT/US00/05224, filed Mar. 1, 2000, which is a continuation of U.S. application Ser. No. 09/260,643, filed Mar. 2, 1999, now U.S. Pat. No. 6,358,201.

BACKGROUND OF THE INVENTION

1. Field of the Invention

The present invention relates to facilitating and providing indications of group coherence in any group environment, such as a gaming, competitive, cooperative or collaborative environment.

2. Background of the Invention

With the growing complexity of life, the relation between physiological conditions and emotional health becomes of increasing interest. Many studies have shown that stress and other emotional factors increase the risk of disease, reduce performance and productivity and severely restrict the quality of life. To this end, the medical communities around the world continually seek remedies and preventive plans. Recently a focus on the self-regulation of systems within the body has led to research in the areas of biofeedback.

Over the last 25 years, a variety of techniques have been introduced as alternatives to more traditional psychotherapies or pharmaceutical interventions for improving mental and/or emotional imbalances, reducing stress and improving performance. Devices have been designed for this purpose, some portable and some not. Portable devices capable of measuring heart rate are known for use in monitoring physical fitness activities, for example.

Another more recent tool is Freeze-Frame®, as disclosed in U.S. Pat. No. 6,358,201 (the '201 Patent), which is hereby incorporated may be used for mental and emotional self-management and performance enhancement. It consists of consciously disengaging the mental and emotional reactions to either external or internal events and then shifting one's center of attention to the physical area around the heart and breathing as if you are breathing through the heart at a rhythm of 5 seconds on the in-breath and 5 seconds on the out-breath as if you are breathing out through the solar plexus. These steps facilitate a shift in the heart's rhythmic beating pattern. The next step is to intentionally shift one's emotional state by focusing on a positive emotion such as love, care or appreciation. In one embodiment, this emotional shift stabilizes the coherent physiological mode and takes the process past what can be achieved with breathing techniques alone.

While the concepts disclosed in the '201 Patent are innovative and groundbreaking, they tend to focus on self-management and performance evaluation in the context of coherence. As such, there is still a need for a system and method for facilitating coherence in a group context.

BRIEF SUMMARY OF THE INVENTION

Disclosed and claimed herein are systems and methods for facilitating group coherence. In one embodiment, a method includes presenting a graphical representation of a scenario to a plurality of individuals, sampling a physiological measure of each of the individuals, and tracking the individuals' heart rhythm patterns using data from said sampled physiological measure. The method further includes determining a current group coherence level for the individuals, where the group coherence level corresponds to a collective degree to which the individuals' heart rhythm patterns exhibit a sine waveform. The method then includes determining an appropriate modification to the scenario based on the current group coherence level, and then presenting an updated graphical representation of the scenario to the individuals, where the updated graphical representation corresponds to the determined appropriate modification.

Other aspects, features, and techniques of the invention will be apparent to one skilled in the relevant art in view of the following detailed description of the invention.

BRIEF DESCRIPTION OF THE DRAWINGS

The features, objects, and advantages of the present invention will become more apparent from the detailed description set forth below when taken in conjunction with the drawings in which like reference characters identify correspondingly throughout and wherein.

DETAILED DESCRIPTION OF EXEMPLARY EMBODIMENTS

I. Overview of the Disclosure

Figure 1A:
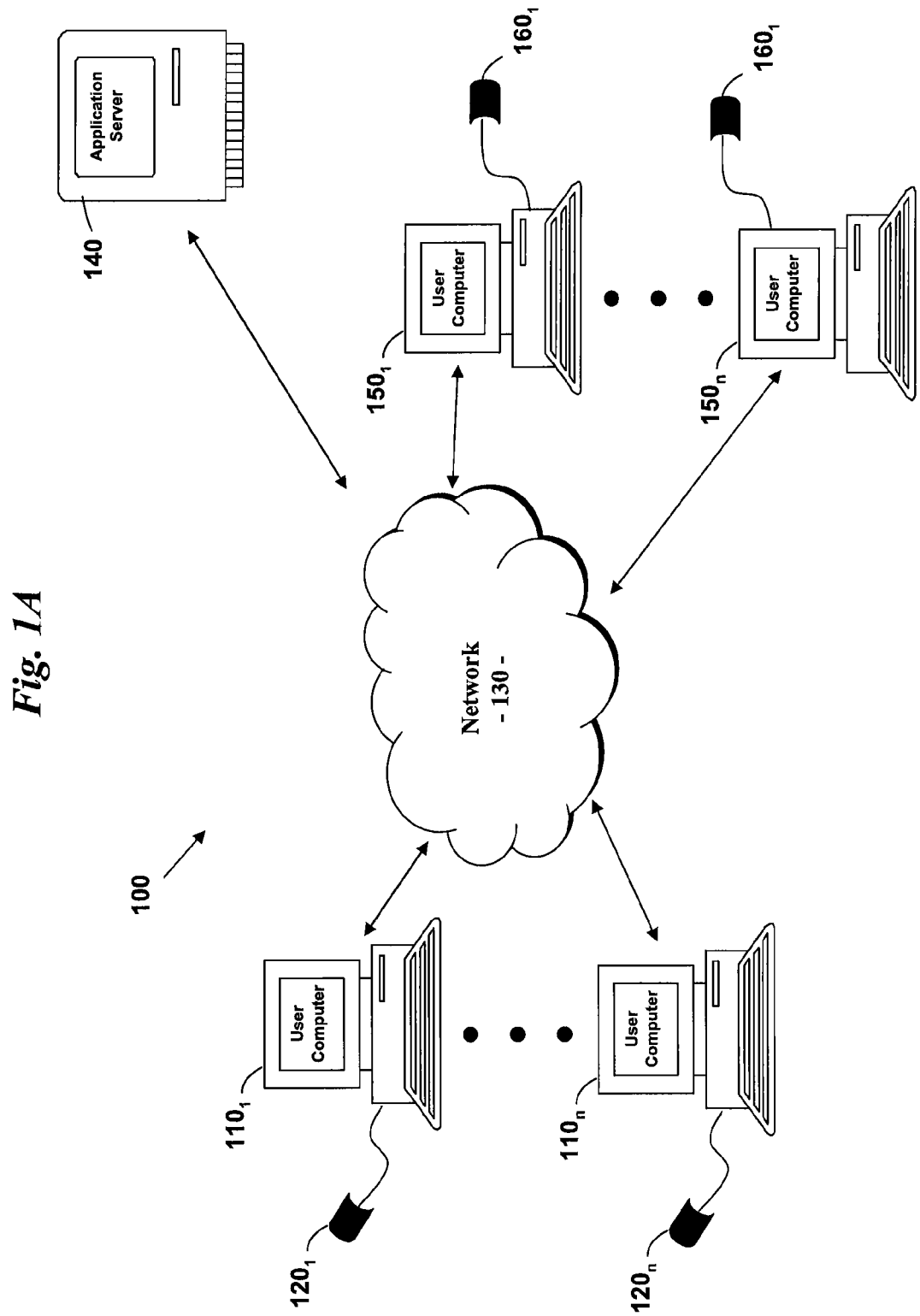
FIG. 1A depicts one embodiment of a system for implementing one or more aspects of the invention.

System and methods for facilitating and providing indications of group coherence are provided. In general terms, one aspect of the invention is to present a graphical representation of a scenario to a plurality of individuals. A physiological measure for each of the plurality of individuals is then sampled. The heart rhythm patterns (and optionally the amplitude of such pattern) for each of the plurality of individuals is tracked using data from said sampling. Thereafter, a current group coherence level for the plurality of individuals or subjects may be determined, wherein the group coherence level corresponds to a collective degree to which said plurality of heart rhythm patterns exhibit a sine waveform (e.g., within a predetermined frequency range), and further optionally based on amplitude characteristics of such pattern (e.g., relative amplitude, changes in amplitude, etc.). In one embodiment, an appropriate modification to the presented scenario may be determined based on the current group coherence level. An updated graphical representation of the scenario may then be presented to the plurality of individuals, wherein the updated graphical representation corresponds to the determined appropriate modification.

The aforementioned aspects of the invention may be implemented in a competitive or gaming environment, for example, which may be implemented as a software-generated scenario or scene in which a user or group(s) of users competes or otherwise interacts with another user (or another group(s) of users) in a graphical environment to achieve or work towards some stated goal or overcome some identified obstacle. For example, in the context of a gaming application, the determined coherence information may be used to modify a gaming scenario in a fashion which indicates the relative degree to which one or more groups of users (or individual users) have successfully traversed the current gaming scenario, where the current gaming scenario corresponds to one or more identified obstacles or challenges.

In another embodiment, the aforementioned aspects of the invention may be implemented in other non-competitive environments, such as facilitating team coherence and performance building contexts. This interaction may be for the purpose of overcoming a predefined set of obstacles, successfully completing one or more predefined goals, or improving a collaboration characteristic. By way of non-limiting examples, facilitating group coherence may relate to corporate teaming and performance building, couples therapy to facilitate communication and emotional connections, work teams, boards, sports teams, etc. In essence, facilitating group coherence may relate to any situation in which more than one individual is desirous of utilizing coherence for improving communication, reducing energy or time consumption, improving synchronization and non-verbal communication skills between team members, increasing team dynamics in decision making, etc.

In one embodiment, physiological properties of an individual (or group of individuals) may be monitored and used as inputs to a group coherence application (e.g., competitive, gaming-oriented, cooperative, etc.). Such monitored physiological properties may include heart rate variability data (heart rate decelerations and accelerations, including both short and long patterns in heart rate decelerations and accelerations), while in other embodiments it may include brain wave activity as measured by an electroencephalogram (EEG), respiration pattern, skin conductance level, etc.

Another aspect of the invention is to utilize one or more physiological properties of one or more individuals as an input to the group coherence application. When implemented in a competitive or gaming environment, the group coherence application may then be used to modify the aforementioned graphical environment in a manner that is reflective of the achieved group coherence level, either on an absolute or relative level. When implemented in a collaborative or cooperative environment, the group coherence application may then be used to provide feedback to the group(s) of users representative of the achieved group coherence level, thereby facilitating the process of achieving a higher level or degree of group coherence.

II. Terminology Overview

Heart rate variability (HRV), derived from an electrocardiogram (ECG), is a measure of the naturally occurring beat-to-beat changes in heart rate. The analysis of HRV, or heart rhythms, provides a powerful, noninvasive measure of neurocardiac function that reflects heart-brain interactions and autonomic nervous system dynamics, which are particularly sensitive to stress and changes in emotional states. Research suggests that there is an important link between emotions and changes in the patterns of both efferent (descending) and afferent (ascending) autonomic activity. These changes in autonomic activity are associated with dramatic changes in the pattern of the heart's rhythm that often occur without any change in the amount of heart rate variability. Specifically, during the experience of negative emotions such as anger, frustration or anxiety, heart rhythms become more erratic and disordered, indicating less synchronization in the reciprocal action that ensues between the parasympathetic and sympathetic branches of the autonomic nervous system (ANS). In short-term (e.g., 3 to 10 seconds) responses to an unpleasant emotional experience, a heart rate deceleration will typically occur in the heart rhythm. In contrast, sustained positive emotions, such as appreciation, love or compassion, are associated with highly ordered or coherent patterns in the heart rhythms, reflecting greater synchronization between the two branches of the ANS, and a shift in autonomic balance toward increased parasympathetic activity. In short-term responses, a pleasant emotional experience may lead to an acceleration in the heart rate.

The term "physiological coherence" may be used herein to describe a number of related physiological phenomena associated with more ordered and harmonious interactions between people, as well as among the body's systems and improved flow of information throughout the psychophysiological networks. By way of analogy, while each member of a jazz band may be performing independently, collectively the band performs to create a harmonious result.

The term coherence has several related definitions. A common definition of the term is "the quality of being logically integrated, consistent, and intelligible," as in a coherent argument. In this context, thoughts and emotional states can be considered "coherent" or "incoherent." Importantly, however, these associations are not merely metaphorical, as different emotions are in fact associated with different degrees of coherence in the oscillatory rhythms generated by the body's various systems.

The term "coherence" is used in physics to describe the ordered or constructive distribution of power within a waveform. The more stable the frequency and shape of the waveform, the higher the coherence. An example of a coherent wave is the sine wave. The term autocoherence is used to denote this kind of coherence. In physiological systems, this type of coherence describes the degree of order and stability in the rhythmic activity generated by a single oscillatory system. One embodiment for computing coherence is disclosed and claimed in the previously-incorporated U.S. Pat. No. 6,358,201.

Coherence also describes two or more waves that are either phase- or frequency-locked. In physiology, coherence may be used to describe a functional mode in which two or more of the body's oscillatory systems, such as respiration and heart rhythms, become entrained and oscillate at the same frequency. The term cross-coherence may be used to specify this type of coherence.

Any one of the above definitions may be applied to the study of both emotional physiology and bioelectromagnetism. Entrainment may be observed between heart rhythms, respiratory rhythms, and blood pressure oscillations.

Another related phenomenon associated with physiological coherence is resonance. In physics, resonance may be used to refer to a phenomenon whereby an unusually large vibration is produced in a system in response to a stimulus whose frequency is identical or nearly identical to the natural vibratory frequency of the system. The frequency of the vibration produced in such a state is said to be the resonant frequency of the system. When the human system is operating in the coherent mode, increased synchronization occurs between the sympathetic and parasympathetic branches of the ANS, and entrainment between the heart rhythms, respiration and blood pressure oscillations may be observed. This occurs because these oscillatory subsystems are all vibrating at the resonant frequency of the system. Most models show that the resonant frequency of the human cardiovascular system is determined by the feedback loops between the heart and brain. In humans and in many animals, the resonant frequency is approximately 0.1 hertz, which is equivalent to a 10-second rhythm.

In short, the term coherence will be used as an umbrella term to describe a physiological mode that encompasses entrainment, resonance, and synchronization—distinct but related phenomena, all of which emerge from the harmonious activity and interactions of the body's subsystems. Correlates of physiological coherence include: increased synchronization between the two branches of the ANS, a shift in autonomic balance toward increased parasympathetic activity, increased heart-brain synchronization, increased vascular resonance, and entrainment between diverse physiological oscillatory systems. The coherent mode is reflected by a smooth, sine wave-like pattern in the heart rhythms (heart rhythm coherence) and a narrow-band, high-amplitude peak in the low frequency range of the heart rate variability power spectrum, at a frequency of about 0.1 hertz.

The inventors hereof have discovered that increased "social coherence" or "group coherence" occurs when a group (family, team, organization) shifts into a new functional mode associated with greatly increased efficiency and effectiveness in communication, co-creative cooperation and output. It has further been discovered that focusing on social or group coherence tends to maximize the freedom of the individual members while maintaining cohesion and resonance within the group. Social coherence is built as members of a group practice increasing their coherence baseline, both individually and collectively. Whether in the context of a sports team, game team, schoolmates or team of co-workers, the group can perform more effectively and efficiently as each individual becomes more coherent and works together as an increasingly coherent team. Increasing social or group coherence enhances intuitive discernment for working together cooperatively and creatively and solving problems together (e.g., non-verbal synchronization, such as the hand signals used in sports for coordinating individual player efforts).

The inventors have scientifically demonstrated that as individual coherence increases, there are numerous benefits in terms of improved health and well-being, improved cognitive and intuitive functions, and improved performance. There are correlated social coherence benefits to groups, teams, families, schools and organizations in terms of improved relationships and communications, improved productivity and outcomes.

As used herein, the terms "a" or "a" shall mean one or more than one. The term "plurality" shall mean two or more than two. The term "another" is defined as a second or more. The terms "including" and/or "having" are open ended (e.g., comprising). The term "or" as used herein is to be interpreted as inclusive or meaning any one or any combination. Therefore, "A, B or C" means any of the following: A; B; C; A and B; A and C; B and C; A, B and C. An exception to this definition will occur only when a combination of elements, functions, steps or acts are in some way inherently mutually exclusive.

When implemented in software, the elements of the invention are essentially the code segments to perform the necessary tasks. The program or code segments can be stored in a processor readable medium, which may include any storage medium, such as a semiconductor memory device, random access memory, read-only memory, flash memory, floppy diskette, a CD-ROM, an optical disk, a hard disk, etc.

As discussed herein, a "computer" or "computer system" is a product including circuitry capable of processing data. The computer system may include, but is not limited to, general purpose computer systems (e.g., server, laptop, desktop, palmtop, personal electronic devices, cellular phone handset, personal digital assistant, personal computers, etc.). In addition, a "communication link" refers to the medium or channel of communication. The communication link may include, but is not limited to, a telephone line, a modem connection, an Internet connection, an Integrated Services Digital Network connection, an Asynchronous Transfer Mode connection, a frame relay connection, an Ethernet connection, a coaxial connection, a fiber optic connection, satellite connections (e.g. Digital Satellite Services, etc.), wireless connections, radio frequency links, electromagnetic links, two way paging connections, etc., and combinations thereof.

Reference throughout this document to "one embodiment," "certain embodiments," "an embodiment" or similar term means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner on one or more embodiments without limitation.

III. Description of the Exemplary Embodiments

One aspect of the invention relates to the fact that there is a point at which the heart rate variability pattern, blood pressure rhythm and respiratory rhythms will entrain. In essence, the system shifts modes and operates at its resonance frequency. As described in the '201 Patent, which is hereby fully incorporated by reference, this frequency is around 0.1 Hz for most people. However, there is a range of frequencies between 0.03125 Hertz and 0.234 Hertz in which the coherent mode can be observed in the majority of people. In terms of respiration, this would mean we would expect the rhythm to vary about one breath per minute around each side of the resonant frequency which is typically a ten second rhythm (0.1 Hertz).

As will be described in more detail below, a subject's coherence level may be determined in accordance with the principles disclosed in the '201 Patent. Once that information is determined, an input signal may be provided to a gaming-oriented application, where such input signal is correlated to the level of coherence the subject achieves. This input signal, or coherence indicator may be used to provide real-time information relating to the level of coherence achieved. In another embodiment, a collective coherence level may similarly be determined and used to provide a composite coherence indicator for a group of individuals.

Referring now to the figures, FIG. 1A depicts one embodiment of a system 100 for implementing one or more embodiments of the invention. In particular, system 100 includes which a first plurality of user computers $110_1$-$110_n$ ("110"), each of which comprises a physiological sensor $120_1$-$120_n$ ("120") configured to detect one or more physiological properties of a human subject. It should be appreciated that there are numerous known means for detecting human physiological properties, including optical pulse monitors (plethysmograph), and ECG sensors or the like. Accordingly, each of the sensors 120 may be configured to be placed onto a subject's finger, clipped to a subject's ear lobe or strapped around the subject using a chest strap configuration, for example. It should be appreciated that numerous other sensor configurations are possible and within the scope of the present disclosure. Additionally, it should be appreciated that the sensor 120 may be integrated with a user computer 110 in the form of a portable electronic device, such as the device disclosed and claimed in U.S. Publication No. 2007/0299354, filed on Jun. 12, 2007 and entitled "Portable Device and Method for Measuring Heart Rate," which application is assigned to the assignee hereof and the contents of which are hereby expressly incorporated by reference.

Each of the first plurality of user computers 110 is configured to communicate over a communication link to a connected network 130 (e.g., Internet). In one embodiment, at least one of the first plurality of user computers 110 accesses the network 130 via a public wireless network connection, such as a WLAN. In this fashion, the first plurality of user computers 110 may communicate with each other, with an application server 140 or with even a second plurality of user computers $150_1$-$150_n$ ("150"). The second plurality of user computers 150 may be similarly equipped with corresponding physiological sensors $160_1$-$160_n$ ("160") configured to detect one or more physiological properties of a human subject, as described in above with reference to sensors 120. In certain embodiments, the user computers 110 and/or 150 may include an application (e.g., browser, client-based gaming application) usable to access an application server 140 using, for example, uniform resource locator (URL) information.

Each of the first plurality of user computers 110 (and user computers 150 when present) may be configured to execute a group or social coherence application, such as a gaming application or cooperative application. Optionally, the application server 140 may be configured to generate and maintain a group environment that is accessible by the first plurality of user computers 110 and/or the second plurality of user computers 150 via the network 130. Physiological data measured and provided by the various sensors (e.g., physiological sensors 120 and/or 160) may be used as user inputs for the group coherence application, such as to drive specific events in the case of a gaming environment.

Each of the first plurality of user computers 110 and/or, the second plurality of user computers 150 may be configured with visual and/or audio output capabilities, including for example the functionality of triggering external devices for the purposes of providing an outward physical indicator (e.g., team meeting indicator). For example, the user computers 110 and/or 150 may include a display in which the current group scenario is graphically displayed to the user. The visual and/or audio outputs may corresponds to events occurring in a group environment generated by the locally-executing group coherence application or by the environment provided by the application server 140. The group environment may correspond to a competitive scenario in which a group of users (or individual users) challenges other users or a group of users (e.g., a subset of the user's of user computers 110 challenges another subset of the users of user computers 110). Alternatively, the group of the users using user computers 110 may challenge another group of users, such as the users of user computers 150.

Figure 1B:
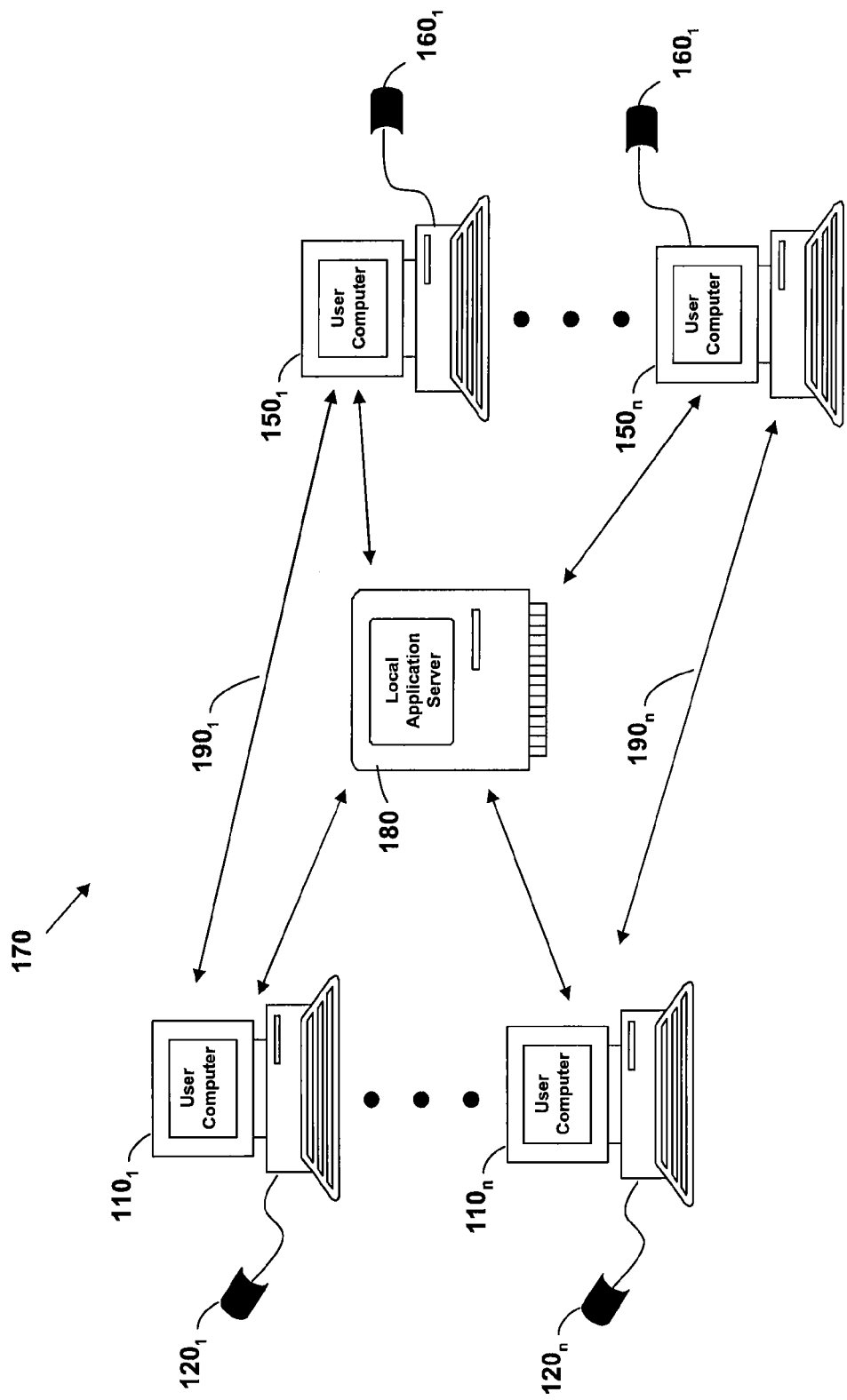
FIG. 1B depicts another embodiment of a system for implementing one or more aspects of the invention.

Referring now to FIG. 1B depicted in another embodiment of a system 170 in which one or more aspects of the invention may be implemented. In particular, the first plurality of user computers 110 are depicted as being configured to communicate with user computers 150 over a direct communication link with the local application server 180, or alternatively directly with each other via communication link $190_1$-$190_n$ ("190"). In this fashion, the aforementioned group coherence application may equally implemented in a "Peer-to-Peer" LAN or WAN in which peers may share their results and may calculate some of the same output for local display. Similarly, the group coherence application may not require a network architecture at all, but instead operate in a local setting (e.g., via direct communication links 190), such as in the case of couples therapy or work group applications.

Figure 2:
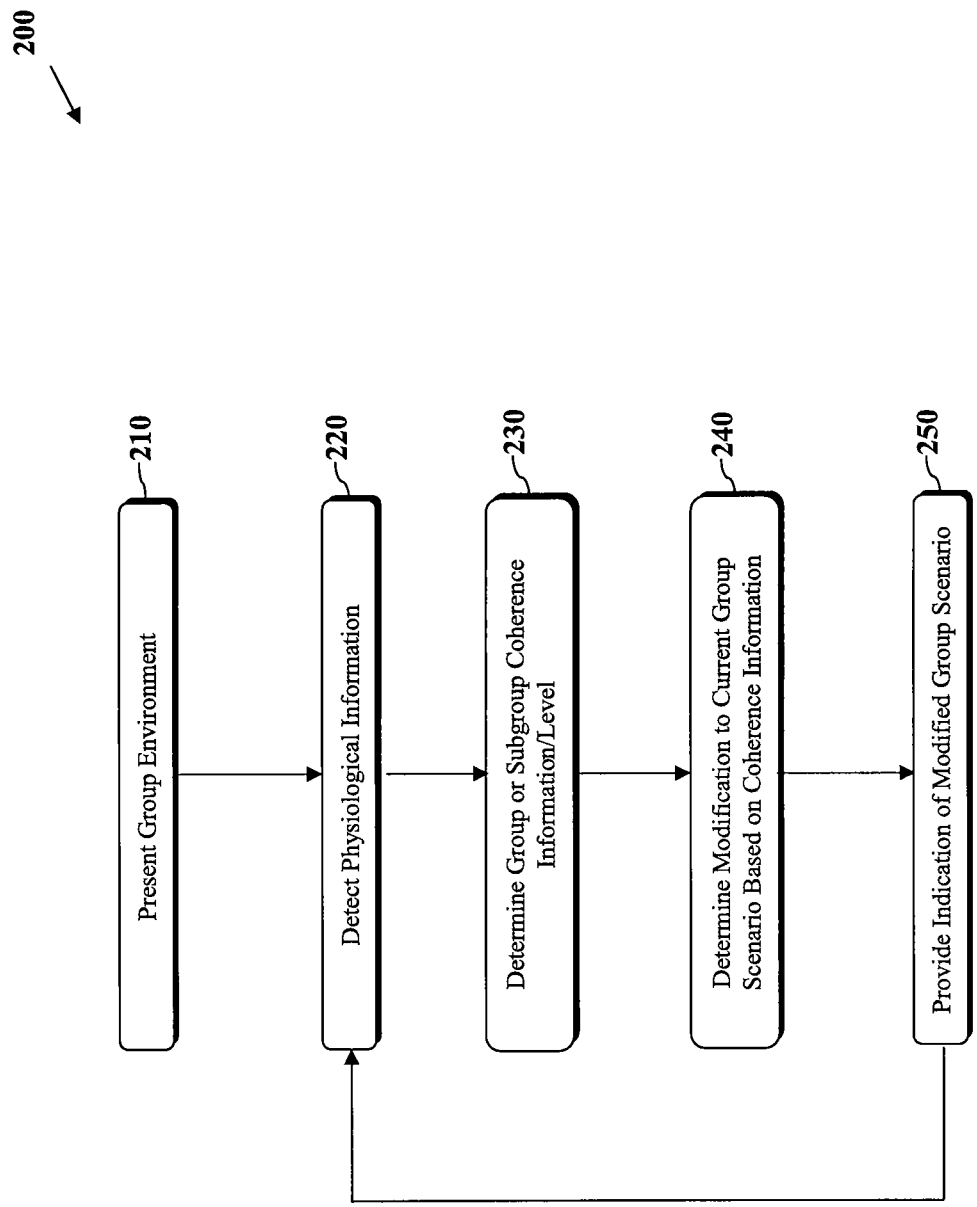
FIG. 2 illustrates one embodiment of a process for implementing certain aspects of the invention in a competitive or gaming environment.

FIG. 2 depicts an embodiment of a process 200 for carrying out one or more aspects of the invention in the context of a competitive or gaming environment. Process 200 begins at block 210 where a group environment (e.g. gaming-oriented environment) may be presented to one or more users, or one or more groups of users (e.g., one or more of the user's of user computers 110 and/or 150). In one embodiment, the group environment may be provided by executing a group coherence program or application on individual user computers 110 and/or 150, or alternatively by such one or more groups of users accessing a group environment generated and presented by the application server 140. It should be appreciated that the group coherence environment may be any software-generated scenario or scene in which a group of user (or groups of users) competes, cooperates or otherwise interacts with another user (or another group of users). This interaction may be for the purpose of overcoming a predefined set of obstacles, successfully completing one or more predefined goals, or improving a collaboration characteristic (e.g., communication, decision making, reducing energy consumption, etc.).

Process 200 may continue to block 220 where physiological information of the individual users being presented with the group environment is detected. In one embodiment, such information may be provided via sensors connected to the individual users in questions, such as sensors 120 or 160 of FIG. 1. Such physiological information may be collected and provided to a computer system, such as application server 140, or alternatively may be provided on a piecemeal basis by each of the user computers 110 and/or 160. As previously mentioned, it should be appreciated that the form of the sensor may be a finger sensor, ear sensor, or any other sensor capable of detecting one or more physiological properties of a human subject. It should be noted that examples of the physiological information that can be analyzed include changes in skin conductance, EEG derivatives (which are evoked potentials where the slope and degree on negativity and onset of the positive shift occur), and heartbeat evoked potentials. Moreover, the derivatives from the ECG or pulse sensors are heart rate accelerations and/or decelerations that may similarly be examined. It should be appreciated that numerous other physiological measures may similarly be examined (e.g., pulse amplitude, blood pressure, etc.).

Continuing to refer to FIG. 2, process 200 may then continue to block 230 where the physiological information detected at block 220 may be used to determine a group coherence state or coherence information for one or more individuals, groups or subgroups of users in the group coherence environment. In one embodiment, the method used to determine and represent the subject's coherence state may be as disclosed in the previously-incorporated '201 Patent. Specifically, the determined group coherence information of block 230 may correspond to an achieved coherence level that is based on a measure of the strength (or relative amplitude) of the highest peak (i.e., coherence peak) within a selected range of the power spectrum distribution (PSD) of the HRV waveform. In general, maximum coherence may be reached when the coherence peak contains a large portion of the total power within the PSD of the HRV waveform.

In another embodiment, the relative amplitude of the coherence peak may be used directed as a measure of the subject's (or group's) level of coherence. While this frequency may be approximately 0.1 Hz, in another embodiment, this resonant frequency may be in the range of between 0.03125 Hertz and 0.234 Hertz. Additionally, it should be appreciated that the coherence peak tends to shift within this coherence range between subjects, and even over time for the same subject. As such, the operation of block 230 may be recursive in nature. The discovery that a subject's state of coherence is a dynamically changing state, means that in one embodiment the coherence peak should be dynamically tracked in order to accurately detect the subject's coherence state. It should further be appreciated that such coherence level may be determined and/or represented in either of the time domain or frequency domain. Additionally, the application server 140 may be charged with computing such group coherence levels, or alternatively this functionality may be performed by one or more other servers, or by the individual user computers 110 and/or 150.

Determining the group coherence information at block 230 may comprise computing an achieved group coherence level for a particular group(s) or subgroup(s) of users in accordance with the techniques disclosed and claimed in the '201 Patent. In one embodiment, the coherence level for each of the individual users that comprise the group or groups in question may be first computed. Once computed, these individual coherence levels then may be averaged together to generate an overall group coherence level. Alternatively, median, weighted averages or any other form of mathematical or numerical combination may be used. It should further be appreciated that the group may even comprise a single subject.

Alternatively, rather than first computing the individual coherence levels for the users that make up the group or groups in question and then combining those coherence levels as described above, in another embodiment the raw detected physiological data from block 220 first may be combined/averaged together, followed by the computation of a coherence state or level based on that combined raw data.

In still another embodiment, a scoring algorithm that accounts for the number of participants and their individual coherence level may be used. For example, a ratio of an actual score (e.g., actual coherence level) to a possible highest score (e.g., highest possible coherence level) may be used. Similarly, quantification based on phase and/or frequency of the time domain physiological signals between individuals (e.g., cross coherence) may be used. In any of the potential quantification techniques employed, such values may be either normalized or absolute.

Continuing to refer to FIG. 2, once the group coherence information or level(s) has been determined as described above, process 200 may then continue to block 240 where the coherence application may then determine how to modify or update a current scenario in the group environment based on the coherence information from block 230. For example, in the context of a gaming application, at block 240 a determination may be made as to how to modify a current gaming scenario in a fashion which indicates the relative degree to which one or more groups of users have successfully traversed the current gaming scenario, where the current gaming scenario corresponds to one or more identified obstacles or challenges. Similarly, the current gaming scenario may correspond to a competitive task which a group of one or more users is engaging in against one or more other users or groups. In essence, the coherence information may be parsed at block 240 in light of what the current group environment calls for, and a determination of how that environment should be modified in response. By way of non-limiting examples, the modification of the current gaming scenario may correspond to a group of one or more users pulling ahead of another group or groups in a racing scenario; ascending to a higher level in a climbing scenario; enlarging a structure in a building scenario, etc.

Process 200 may then continue to block 250 where an indication or output may be provided to the group or groups of one or more users in the group environment representative or corresponding to the group scenario modification that occurred at block 240. In this fashion, such indication may be a visual and/or audio representation of the modification from block 240. For example, where the gaming scenario is being presented on a display of a user computer (e.g., user computers 110), the indication may be in the form of an updated scene reflecting the relative success of the user (or group of users) against their competition. Similarly, the feedback may be in the form of music, haptic, visual, etc. It should further be appreciated that such feedback may be provided using an outwardly physical device.

In certain embodiments, the aforementioned group coherence application may be implemented in a virtual reality environment. In such cases, the indication or output of block 250 may correspond to some change in the virtual environment (e.g., changes in physical characteristics of a virtual persona, location within the virtual environment, etc.).

While in certain embodiments the group or groups of one or more users having the highest achieved level of coherence may correspond to the winner of the game or competition, in other embodiments it may be desirable to designate the victor using some other criteria, such as the longest sustained level of coherence, some combination of the achieved level of coherence and the amount of time such level is sustained, or a scenario-dependent or scenario-weighted coherence level achieved (e.g., coherence may be more difficult to achieve in some gaming scenarios than in others).

Figure 3:
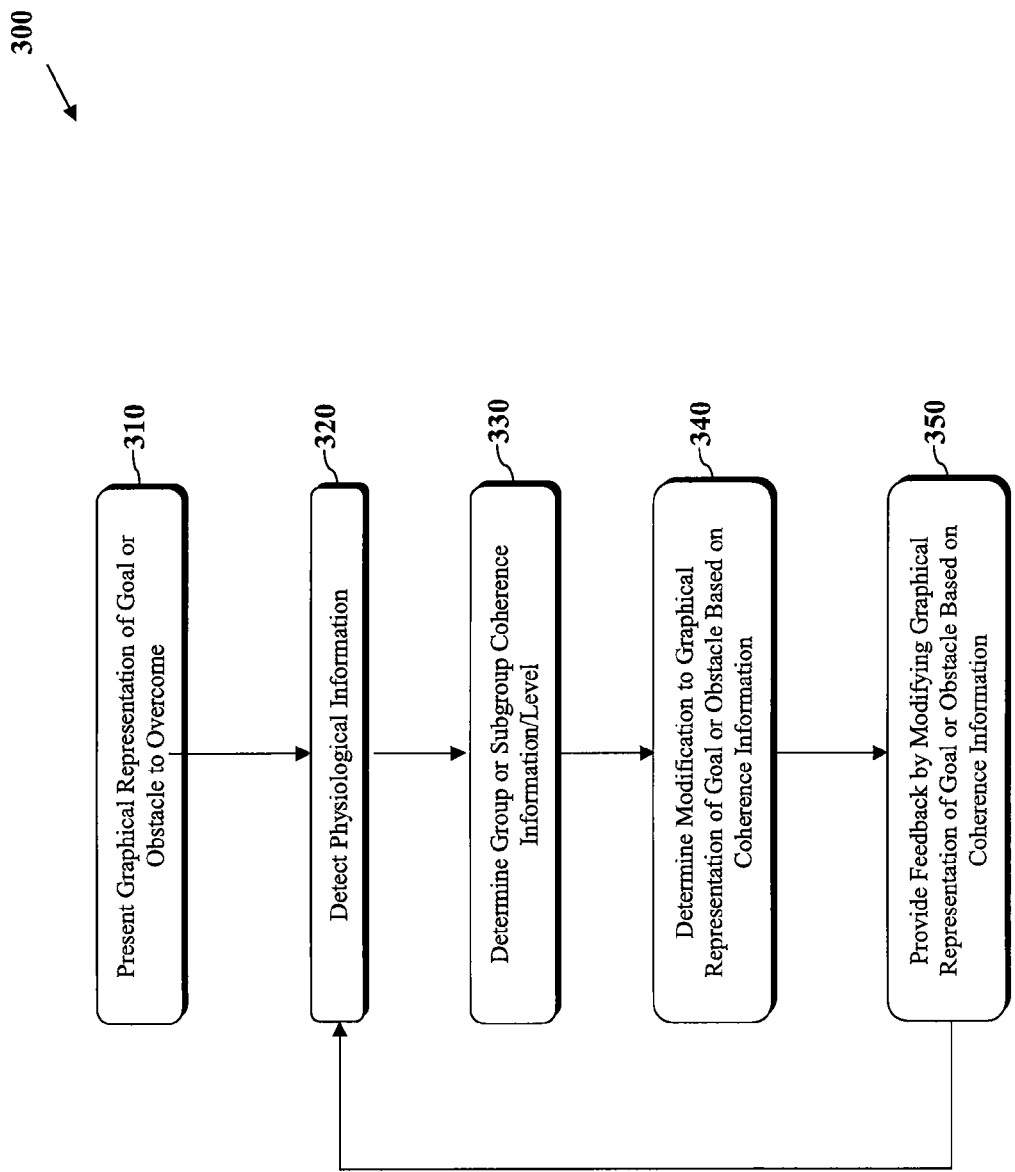
FIG. 3 illustrates another embodiment of a process for implementing certain aspects of the invention in a collaborative or cooperative environment.

Referring now to FIG. 3, depicted is an embodiment of a process 300 for carrying out one or more aspects of the invention in the context of a collaborative or cooperative environment. Process 300 begins at block 310 where a graphical representation of a goal or obstacle to overcome may be presented to one or more groups of users (e.g., one or more of the user's of user computers 110 and/or 150). In one embodiment, the graphical representation may be provided by executing a group coherence program or application on one or more of the individual user computers 110 and/or 150, or alternatively by such one or more groups of users accessing the application server 140. It should be appreciated that the group coherence environment may be any software-generated graphical scene or image representing a goal that the particular group(s) of one or more users are working towards achieving, a particular obstacle that such users are endeavoring to overcome, or even a particular problem to be solved. By way of providing non-limiting example, this graphical representation may be in the form of raising/lowering the displayed temperature on a thermometer; opening/closing a door or gate to move to a new level or area; moving or controlling a paddle in a game (e.g., tennis, ping pong, etc.); controlling the location, orientation or movement of any displayed item; turning a fan or other propulsion device on or off to effect movement on an object, such as a ball; climbing or descending a mountain; running; walking; driving a car; etc.

Process 300 may continue to block 320 where physiological information of the individual users being presented with the graphical representation may be detected. As with the embodiment of FIG. 2, such information may be provided via sensors connected to the individual users in questions, such as sensors 120 or 160 of FIG. 1. For brevity, the operations and aspects of the invention set forth above with respect block 220 of FIG. 2 is incorporated herein and equally relates to block 320 of FIG. 3.

Continuing to refer to FIG. 3, process 300 may then continue to block 330 where the physiological information detected at block 320 may be used to determine a group coherence state or coherence information for the group(s) of one or more users being presented with the graphical representation. In one embodiment, the method used to determine and represent the subject's coherence state may be as disclosed in the previously-incorporated '201 Patent. Specifically, and as described above with reference to block 230 of FIG. 2, the determined group coherence information of block 330 may correspond to an achieved coherence level that is based on a measure of the strength (or relative amplitude) of the highest peak (i.e., coherence peak) within a selected range of the power spectrum distribution (PSD) of the HRV waveform. In general, maximum coherence may be reached when the coherence peak contains a large portion of the total power within the PSD of the HRV waveform.

In another embodiment, the relative amplitude of the coherence peak may be used directed as a measure of the subject's (or group's) level of coherence. While this frequency may be approximately 0.1 Hz, in another embodiment, this resonant frequency may be in the range of between 0.03125 Hertz and 0.234 Hertz. Additionally, it should be appreciated that the coherence peak tends to shift within this coherence range between subjects, and even over time for the same subject. As such, the operation of block 330 may be recursive in nature. As previously described, the fact that a subject's state of coherence is a dynamically changing state, requires that the coherence peak be dynamically tracked in order to accurately detect the subject's coherence state. It should further be appreciated that such coherence level may be determined and/or represented in either of the time domain or frequency domain. Additionally, the application server 140 may be charged with computing such group coherence levels, or alternatively this functionality may be performed by one or more other servers, or by the individual user computers 110 and/or 150.

As with the embodiment described above with reference to block 230 of FIG. 2, determining the group coherence information at block 330 may comprise computing an achieved group coherence level for a particular group or groups of one or more users in accordance with any aspects of the techniques disclosed and claimed in the '201 Patent. In one embodiment, the coherence level for each of the individual users that comprise the group or groups in question may be first computed. Once computed, these individual coherence levels then may be averaged together to generate an overall group coherence level. Alternatively, median, weighted averages or any other form of mathematical or numerical combination may be used.

Alternatively, rather than first computing the individual coherence levels for the users that make up the group or groups in question and then combining those coherence levels as described above, in another embodiment the raw detected physiological data from block 320 first may be combined/averaged together, followed by the computation of a coherence state or level based on that combined raw data.

In still another embodiment, a scoring algorithm that accounts for the number of participants and their individual coherence level may be used. For example, a ratio of an actual score (e.g., actual coherence level) to a possible highest score (e.g., highest possible coherence level) may be used. Similarly, quantification based on phase and/or frequency of the time domain physiological signals between individuals (e.g., cross coherence) may be used. In any of the potential quantification techniques employed, such values may be either normalized or absolute.

Continuing to refer to FIG. 3, once the group coherence information or level(s) has been determined as described above, process 300 may then continue to block 340 where the coherence application may then determine how to modify or update the graphical representation of the goal/obstacle based on the coherence information from block 330. For example, as the group(s) of one or more users achieves a higher level of coherence, it may be determined at block 340 that the graphical representation of the goal/obstacle should be updated to reflect the fact that the goal is closer to being achieved, or that the obstacle is closer to being overcome. Alternatively, if the group(s) of one or more users fails to achieve a higher level of coherence, or in fact becomes less coherent, it may be determined at block 340 that the graphical representation of the goal/obstacle should be equally updated to reflect this fact by showing the goal as being further away or that the obstacle larger. It should of course be understood that the possible variations on what form the graphical representation may take, as well as how that form may be modified, are nearly infinite. For purposes of the scope of this disclosure, any graphical representation and modification thereof capable of providing feedback to a group of users, where the feedback corresponds to the achieved level of group coherence would be consistent with the principles of the invention and considered within the scope of this disclosure.

Once the group coherence application determines how the modify or otherwise update the graphical representation, process 300 may then continue to block 350 where the updated or modified graphical representation may then be presented to the group or groups of one or more users as feedback (e.g., displaying the updated or modified graphical representation on a display of a user computer, such as user computers 110 and/or 150).

In certain embodiments, the aforementioned group coherence application may be implemented in a virtual reality environment, where a scene or environment corresponds to the graphical representation of the goal to achieve or obstacle to overcome. Additionally, the feedback to be provided at block 350 may correspond to any indication representative of success or amount of desired benefit obtained.

It should generally be appreciated that the process 300 of FIG. 3 may correspond to any cooperative or collaborative environment in which a group of one or more individuals collaboratively uses coherence for some shared purpose (e.g., facilitate communication and emotional connections, reducing energy or time consumption, improving synchronization, increasing decision making, etc.)

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A method for facilitating group coherence comprising:
   presenting a graphical representation of a scenario to a plurality of individuals;
   sampling a physiological measure of each of the plurality of individuals;
   tracking a plurality of heart rhythm patterns corresponding to each of the plurality of individuals using data from said sampling;
   determining a current group coherence level for the plurality of individuals, wherein the current group coherence level is based on individual coherence levels computed for the plurality of individuals, and wherein the group coherence level corresponds to a collective degree to which the plurality of heart rhythm patterns exhibit a sine waveform;
   determining an appropriate modification to the scenario based on the current group coherence level; and presenting an updated graphical representation of the scenario to the group, wherein the updated graphical representation corresponds to the determined appropriate modification.

2. The method of claim 1, wherein the group coherence level further corresponds to corresponding amplitude characteristics of the plurality of heart rhythm patterns.

3. The method of claim 1, wherein the graphical representation of the scenario is an online virtual reality environment.

4. The method of claim 1, wherein the scenario corresponds to a gaming environment in which the plurality of individuals are in competition with each other.

5. The method of claim 1, wherein the scenario corresponds to a gaming environment in which the plurality of individuals are in competition with one or more additional groups of individuals.

6. The method of claim 1, wherein the graphical representation corresponds to at least one of a desired goal and an obstacle to overcome.

7. The method of claim 6, wherein the scenario corresponds to a collaborative environment in which the plurality of individuals are cooperating with each other for at least one of achieving the desired goal and overcoming the obstacle.

8. The method of claim 1, wherein presenting the graphical representation comprises displaying the scenario on a plurality of user computers corresponding to each of the plurality of individuals.

9. The method of claim 1, performed by a group coherence application executing on a server, wherein the server is networked with one or more user computers of the plurality of individuals.

10. The method of claim 1, wherein the current group coherence level is a first group coherence level corresponding to a first group of individuals, and the method further comprising:
determining a second group coherence level corresponding to a second group of individuals; and
updating the graphical representation of the scenario based on both the first group coherence level and the second group coherence level.

11. The method of claim 1, wherein each of the plurality of heart rhythm patterns has an amplitude and frequency which varies over time.

12. The method of claim 1, wherein the group coherence level corresponds to the collective degree to which the plurality of heart rhythm patterns exhibit the sine waveform within a frequency range of between 0.03125 Hertz and 0.234 Hertz.

13. The method of claim 1, wherein presenting the updated graphical representation comprises providing feedback to the plurality of individuals that is representative of the current group coherence level.

14. The method of claim 1, wherein sampling the physiological measure comprises sampling the physiological measure where said physiological measure comprises respiratory sinus arrhythmia, heart rate variability, respiration patterns and blood pressure rhythms.

15. The method of claim 1, wherein sampling further comprises analyzing the physiological measure for the plurality of individuals in one of a frequency domain, a time domain, a period analysis and a template match.

16. The method of claim 1 wherein the modification to the scenario includes changes to an online virtual reality environment including at least one of changing a door closure status, moving a game paddle, changing a propulsion device activation status to effect movement of an object, altering altitude on a mountain, running, walking, and driving a car.

17. The method of claim 1, wherein the modification to the scenario includes at least one of a group of users pulling ahead of another group in a racing scenario, the group of users ascending to a higher level in a climbing scenario, the group of users enlarging a structure in a building scenario, changes in physical characteristics of a virtual persona, and changes of location within a virtual environment.

18. The method of claim 1, wherein the plurality of individuals includes at least one of a team and a couple.

19. A system for facilitating group coherence comprising:
a sensor configured to sample a physiological measure of each of a plurality of individuals; and
an application server executing a group coherence application configured to:
present a graphical representation of a scenario to the plurality of individuals on one or more user computers,
track a plurality of heart rhythm patterns corresponding to each of the plurality of individuals using data received from the sensor,
determine a current group coherence level for the plurality of individuals, wherein the current group coherence level is based on individual coherence levels computed for the plurality of individuals, and wherein the group coherence level corresponds to a collective degree to which the plurality of heart rhythm patterns exhibit a sine waveform,
determine an appropriate modification to the scenario based on the current group coherence level, and
present an updated graphical representation of the scenario to the plurality of individuals on the one or more user computers, wherein the updated graphical representation corresponds to the determined appropriate modification.

20. The system of claim 19, wherein the group coherence level further corresponds to corresponding amplitude characteristics of the plurality of heart rhythm patterns.

21. The system of claim 19, wherein the graphical representation of the scenario is an online virtual reality environment.

22. The system of claim 19, wherein the scenario corresponds to a gaming environment in which the plurality of individuals are in competition with each other.

23. The system of claim 19, wherein the scenario corresponds to a gaming environment in which the plurality of individuals are in competition with one or more additional groups of individuals.

24. The system of claim 19, wherein the graphical representation corresponds to at least one of a desired goal and an obstacle to overcome.

25. The system of claim 24, wherein the scenario corresponds to a collaborative environment in which the plurality of individuals are cooperating with each other for at least one of achieving the desired goal and overcoming the obstacle.

26. The system of claim 19, wherein the application server is coupled to the one or more user computers over a network connection.

27. The system of claim 19, wherein the one or more user computers includes the application server.

28. The system of claim 19, wherein the current group coherence level is a first group coherence level corresponding to a first group of individuals, and wherein the group coherence application is further to:
determine a second group coherence level corresponding to a second group of individuals, and update the graphical representation of the scenario based on both the first group coherence level and the second group coherence level.

29. The system of claim 19, wherein each of the plurality of heart rhythm patterns has an amplitude and frequency which varies over time.

30. The system of claim 19, wherein the group coherence level corresponds to the collective degree to which the plurality of heart rhythm patterns exhibit the sine waveform within a frequency range of between 0.03125 Hertz and 0.234 Hertz.

31. The system of claim 19, wherein the group coherence application is to present the updated graphical representation to the plurality of individuals as feedback representative of the current group coherence level.

32. The system of claim 19, wherein the physiological measure comprises at least one of respiratory sinus arrhythmia, heart rate variability, respiration patterns and blood pressure rhythms.

33. The system of claim 19, wherein the sensor further analyzes the physiological measure for the plurality of individuals in one of a frequency domain, a time domain, a period analysis and a template match.

34. The system of claim 19, wherein the graphical representation includes at least one of music feedback, haptic feedback, and visual feedback including at least one of a numerical-display of the group coherence level, a displayed temperature on a thermometer, and controlling at least one of the location, orientation, and movement of a displayed item.

35. The system of claim 19 wherein the modification to the scenario includes changes to an online virtual reality environment including at least one of changing a door closure status, moving a game paddle, changing a propulsion device activation status to effect movement of an object, altering altitude on a mountain, running, walking, and driving a car.

36. The system of claim 19, wherein the modification to the scenario includes at least one of a group of users pulling ahead of another group in a racing scenario, the group of users ascending to a higher level in a climbing scenario, the group of users enlarging a structure in a building scenario, changes in physical characteristics of a virtual persona, and changes of location within a virtual environment.

37. The system of claim 19, wherein the plurality of individuals includes at least one of a team and a couple.

38. The method of claim 1, wherein the graphical representation includes at least one of music feedback, haptic feedback, and visual feedback including at least one of a numerical display of the group coherence level, a displayed temperature on a thermometer, and controlling at least one of the location, orientation, and movement of a displayed item.

39. A method for facilitating group coherence comprising:

presenting a graphical representation of a scenario to a plurality of individuals;

sampling a physiological measure of each of the plurality of individuals;

tracking a plurality of heart rhythm patterns corresponding to each of the plurality of individuals using data from said sampling, wherein coherence peaks are tracked to detect coherence states for the plurality of individuals;

determining a current group coherence level for the plurality of individuals, wherein the current group coherence level is based on individual coherence levels computed for the plurality of individuals, and wherein the group coherence level corresponds to a collective degree to which the plurality of heart rhythm patterns exhibit a sine waveform;

determining an appropriate modification to the scenario based on the current group coherence level; and presenting an updated graphical representation of the scenario to the group, wherein the updated graphical representation corresponds to the determined appropriate modification.

\* \* \* \* \*